US011890416B2

United States Patent
Eger et al.

(10) Patent No.: US 11,890,416 B2
(45) Date of Patent: Feb. 6, 2024

(54) PROCESS AND SIGNAL PROCESSING UNIT FOR DETERMINING A PNEUMATIC PARAMETER WITH THE USE OF A LUNG-MECHANICAL MODEL AND OF A GRADIENT MODEL

(71) Applicant: Drägerwerk AG & Co. KGaA, Lübeck (DE)

(72) Inventors: Marcus Eger, Lübeck (DE); Philipp Rostalski, Lübeck (DE); Eike Petersen, Lübeck (DE); Jan Grasshoff, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 509 days.

(21) Appl. No.: 17/142,762

(22) Filed: Jan. 6, 2021

(65) Prior Publication Data
US 2021/0205561 A1 Jul. 8, 2021

(30) Foreign Application Priority Data
Jan. 7, 2020 (DE) ...................... 10 2020 000 014.2

(51) Int. Cl.
*A61M 16/00* (2006.01)
*A61B 5/00* (2006.01)
(Continued)

(52) U.S. Cl.
CPC ........... *A61M 16/026* (2017.08); *A61B 5/087* (2013.01); *A61B 5/0809* (2013.01);
(Continued)

(58) Field of Classification Search
CPC .......... A61M 16/0057; A61M 16/0066; A61M 16/0069; A61M 16/024; A61M 16/026;
(Continued)

(56) References Cited

U.S. PATENT DOCUMENTS

| 6,588,423 B1 | 7/2003 | Sinderby |
| 7,021,310 B1 | 4/2006 | Sinderby et al. |

(Continued)

FOREIGN PATENT DOCUMENTS

| CN | 105579087 A | 5/2016 |
| CN | 107205694 A | 9/2017 |

(Continued)

OTHER PUBLICATIONS

M. Ungureanu and W. M. Wolf: "Basic Aspects Concerning the Event-Synchronous Interference Canceller," IEEE Transactions on Biomedical Engineering, vol. 53, No. 11 (2006), pp. 2240-2247.

(Continued)

*Primary Examiner* — Joseph D. Boecker
(74) *Attorney, Agent, or Firm* — McGlew and Tuttle, P.C.

(57) ABSTRACT

A process and a signal processing unit determine a pneumatic parameter ($P_{mus}$) for the spontaneous breathing of a patient. The patient is ventilated mechanically by a ventilator. A lung-mechanical model (20) and a gradient model (22) are preset. The lung-mechanical model (20) describes a relationship between the pneumatic parameter ($P_{mus}$) as well as a volume flow signal (Vol'), a volume signal (Vol) and/or a respiratory signal (Sig), which can be measured. The gradient model (22) describes a value for the pneumatic parameter ($P_{mus}$) as a function of N chronologically earlier values of the pneumatic parameter ($P_{mus}$) or of a variable correlating with the pneumatic parameter ($P_{mus}$). N values for the correlating variable are determined at first. At least one additional value is subsequently determined for the pneumatic parameter ($P_{mus}$). N chronologically earlier values of the correlating variable, current signal values, the lung-mechanical model (20) and the gradient model (22) are used for this purpose.

20 Claims, 4 Drawing Sheets

(51) Int. Cl.
*A61B 5/087* (2006.01)
*A61B 5/389* (2021.01)
*A61B 5/11* (2006.01)
*A61B 5/08* (2006.01)
*G16H 40/63* (2018.01)
*G16H 50/50* (2018.01)

(52) U.S. Cl.
CPC ............ *A61B 5/1107* (2013.01); *A61B 5/389* (2021.01); *A61B 5/6847* (2013.01); *A61B 5/725* (2013.01); *A61M 16/0057* (2013.01); *A61M 16/024* (2017.08); *G16H 40/63* (2018.01); *G16H 50/50* (2018.01); *A61B 2562/0247* (2013.01); *A61B 2562/04* (2013.01); *A61M 2016/0027* (2013.01); *A61M 2016/0036* (2013.01); *A61M 2230/42* (2013.01); *A61M 2230/60* (2013.01)

(58) Field of Classification Search
CPC .. A61M 2016/0027; A61M 2016/0036; A61M 2230/60; A61B 5/0803; A61B 5/0809; A61B 5/087; A61B 5/1107; A61B 5/6847; A61B 5/725; G16H 40/63; G16H 50/50

See application file for complete search history.

(56) References Cited

U.S. PATENT DOCUMENTS

| | | | |
|---|---|---|---|
| 8,109,269 B2 | 2/2012 | Eger | |
| 8,950,399 B2 | 2/2015 | Handzsuj et al. | |
| 9,114,220 B2 | 8/2015 | Masic | |
| 2002/0056454 A1 | 5/2002 | Samzelius | |
| 2008/0234595 A1 | 9/2008 | Ranieri et al. | |
| 2008/0257349 A1* | 10/2008 | Hedner | G16H 20/40 128/204.23 |
| 2008/0308104 A1 | 12/2008 | Blomberg | |
| 2009/0114224 A1 | 5/2009 | Handzsuj et al. | |
| 2010/0071696 A1 | 3/2010 | Jafari | |
| 2010/0252038 A1 | 10/2010 | Lagerborg | |
| 2011/0290252 A1* | 12/2011 | Amjad | A61M 16/026 128/204.23 |
| 2011/0301482 A1 | 12/2011 | Sinderby | |
| 2013/0276788 A1 | 10/2013 | Masic | |
| 2016/0008559 A1* | 1/2016 | Tiedje | A61B 5/113 128/204.23 |
| 2016/0136370 A1 | 5/2016 | Heesch et al. | |
| 2016/0310069 A1* | 10/2016 | Sinderby | A61B 5/7207 |
| 2017/0128684 A1 | 5/2017 | Sinderby et al. | |
| 2017/0224234 A1* | 8/2017 | Ahlmen | A61M 16/024 |
| 2018/0001041 A1 | 1/2018 | Albanese et al. | |
| 2018/0177963 A1* | 6/2018 | Wang | A61B 5/085 |
| 2018/0279963 A1 | 10/2018 | Vicario et al. | |
| 2018/0317808 A1 | 11/2018 | Wang et al. | |
| 2018/0344194 A1* | 12/2018 | Eger | A61B 5/7289 |
| 2019/0246952 A1* | 8/2019 | Groenendaal | A61B 5/0826 |
| 2019/0254566 A1 | 8/2019 | Albanese et al. | |
| 2019/0351166 A1 | 11/2019 | Hallback | |
| 2020/0360690 A1* | 11/2020 | Evans | G16H 20/40 |
| 2021/0205558 A1* | 7/2021 | Vicario | A61B 5/4836 |

FOREIGN PATENT DOCUMENTS

| | | |
|---|---|---|
| CN | 108135536 A | 6/2018 |
| CN | 109350063 A | 2/2019 |
| CN | 109906054 A | 6/2019 |
| DE | 102007062214 B3 | 8/2009 |
| DE | 102015015296 A1 | 6/2017 |
| EP | 1056499 B1 | 11/2004 |
| EP | 1205202 B1 | 6/2007 |
| WO | 9722377 A1 | 6/1997 |
| WO | 2006131149 A1 | 12/2006 |
| WO | 2008131798 A1 | 11/2008 |
| WO | 2017055959 A1 | 4/2017 |
| WO | 2018143844 A1 | 8/2018 |

OTHER PUBLICATIONS

Hartikainen, J. and Särkkä, S.: "Kalman filtering and smoothing solutions to temporal Gaussian process regression models," in: Proceedings of IEEE International Workshop on Machine Learning for Signal Processing (MLSP), 2010.

Sinderby, C. et. al.: "Is one fixed level of assist sufficient to mechanically ventilate spontaneously breathing patients?", Yearbook of Intensive Care and Emergency Medicine, 2007, Springer,348-367.

Sinderby, C. et. al.: "Inspiratory Muscle Unloading by Neurally Adjusted Ventilatory Assist During Maximal Inspiratory Efforts in Healthy Subjects", Chest 2007, vol. 131, pp. 711-717.

Sinderby, C. et. al.: "Neural control of mechanical ventilation in respiratory failure", Nature Medicine 1999 (5)12: 1433-1436.

Younes, M.: "Proportional assist ventilation" in: Tobin M. J., ed. "Principles and practice of mechanical ventilation", New York, NY: McGraw-Hill, 1994; pp. 349-369.

Saatci, Esra et. al.: Dual Unscented Kalman Filter and its Applications to Respiratory System Modelling, in: Kalman Filter: Recent Advances and Applications, edited by: Victor M. Moreno and Alberto Pigazo, pp. 584, Apr. 2009.

Fresnel, E. et al.: "Realistic human muscle pressure for driving a mechanical lung", EPJ Nonlinear Biomedical Physics 2014, 2:7.

Jodat, R. W. et al.: "Simulation of respiratory mechanics", Biophys J. Nov. 1966;6(6):pp. 773-785.

Solin, A. & Särkkä, S.: "Explicit Link Between Periodic Covariance Functions and State Space Models", Proceed. 17th Internat. Conf. Artificial Intelligence and Statistics (AISTATS) JMLR vol. 33, pp. 904-912.

Hickling, Keith G. "The pressure-volume curve is greatly modified by recruitment: a mathematical model of ARDS lungs" American journal of respiratory and critical care medicine 158.1 (1998): pp. 194-202.

Saatci, E. and Akan, A.: "Lung model parameter estimation by unscented Kalman filter", Proc 29th Conf IEEE Eng Med Biol Soc. 2007;2007:2556-2559.

\* cited by examiner

PROCESS AND SIGNAL PROCESSING UNIT FOR DETERMINING A PNEUMATIC PARAMETER WITH THE USE OF A LUNG-MECHANICAL MODEL AND OF A GRADIENT MODEL

CROSS REFERENCE TO RELATED APPLICATIONS

This application claims the benefit of priority under 35 U.S.C. § 119 of German Application 10 2020 000 014.2, filed Jan. 7, 2020, the entire contents of which are incorporated herein by reference.

TECHNICAL FIELD AND BACKGROUND

The present invention pertains to a computer-implemented process and to a signal processing unit, which is configured to automatically determine a pneumatic parameter. This pneumatic parameter to be determined is correlated with the spontaneous breathing (the intrinsic breathing activity) of a patient, the patient preferably being ventilated mechanically by means of a ventilator at least from time to time. Knowledge of the pneumatic parameter can be used especially to automatically synchronize the operation of the ventilator with the spontaneous breathing of the mechanically ventilated patient and/or in order to detect anomalies in the spontaneous breathing of the patient.

SUMMARY

The basic object of the present invention is to provide a process and a signal processing unit, which are capable of automatically determining a pneumatic parameter better than prior-art processes and signal processing units can, wherein the pneumatic parameter to be determined describes the spontaneous breathing of a patient or is correlated with this spontaneous breathing and wherein the patient is preferably ventilated mechanically by a ventilator at least from time to time.

The present invention is accomplished by a process having the features of claim 1 and by a signal processing unit having the features of claim 10. Advantageous embodiments are described in the subclaims. Advantageous embodiments of the process according to the present invention are also advantageous embodiments of the signal processing unit according to the present invention and vice versa, insofar as meaningful.

The computer-implemented process according to the present invention as well as the data-processing signal processing unit according to the present invention are capable of automatically determining a pneumatic parameter at least approximately. This pneumatic parameter describes the spontaneous breathing (intrinsic breathing activity) of a patient or is correlated with the spontaneous breathing of the patient. This patient is ventilated mechanically by means of a ventilator or anesthesia device at least from time to time. The spontaneous breathing is an intrinsic breathing activity of the patient and it is then superimposed to the mechanical ventilation.

A computer-accessible and hence computer-analyzable lung-mechanical model as well as a computer-accessible and hence computer-analyzable gradient model are preset for the process. The signal processing unit has read access at least from time to time to a memory, in which this lung-mechanical model and this gradient model are stored in a computer-analyzable manner.

The lung-mechanical model describes at least one relationship, and optionally a plurality of relationships, between
 the pneumatic parameter $P_{mus}$ to the determined and
 a volume flow signal Vol' and/or a volume signal Vol and/or a measurable pneumatic pressure signal for the pressure $P_{aw}$ in the airways and/or for the pressure $P_{es}$ in the esophagus of the patient and/or a respiratory signal Sig.

The volume flow signal Vol' is correlated with the flow of breathing air to and/or from the lungs of the patient. This flow is generated by the spontaneous breathing and by the mechanical ventilation. The volume signal Vol is correlated with the filling level of the patient's lungs, which is variable over time. The pneumatic pressure signals $P_{aw}$ and $P_{es}$ are correlated with the pressure in the airways and in the esophagus of the patient and can be measured by means of at last one suitable sensor. The respiratory signal Sig is a parameter for the spontaneous breathing of the patient and can be generated with the use of measured values of at least one sensor. Especially a sensor array on the skin of the patient or a sensor in front of the airways and/or a sensor in the body, for example, in the esophagus close to the diaphragm or in the trachea or in the stomach of the patient is used as the sensor for the respiratory signal. The respiratory signal Sig is especially an EMG (electromyography) signal or an MMG (mechanomyographic) signal. It is also possible that images of an optical signal are analyzed in order to generate a respiratory signal Sig.

The lung-mechanical model may depend on additional input variables, which can be measured or determined in another manner.

The gradient model describes a value of the pneumatic parameter $P_{mus}$ to be determined for a scanning time as a function of N values of a variable, which is variable over time and is correlated with the pneumatic parameter $P_{mus}$, for N previous scanning times. Here, N is a preset number and is greater than or equal to 1.

The correlating variable occurring in the gradient model may be the pneumatic parameter $P_{mus}$ itself or a variable that depends on the pneumatic parameter $P_{mus}$ or is correlated in another manner with the pneumatic parameter $P_{mus}$.

It is possible that the preset gradient model refers to two or even more different correlating variables, e.g., to the pneumatic parameter $P_{mus}$ and to another correlating variable, which is correlated with the pneumatic parameter $P_{mus}$. It is also possible that the gradient model takes into account the fact that the spontaneous breathing is a periodic process. The amplitude and the phase of this periodic process are used as two variables of the gradient model that are correlated with the pneumatic parameter $P_{mus}$, and the frequency, variable over time, of the spontaneous breathing, which is assumed to be periodic, is used additionally in one embodiment. The gradient model may comprise at least one additional function, which sets the value of a correlating variable at a scanning time as a function of values of this correlating variable or of at least one other correlating variable at earlier scanning times.

The signal processing unit generates respective signal values for at least one signal and preferably for each signal to which the lung-mechanical model refers. In order to generate signal values, the signal processing unit carries out at least one of the following steps, and optionally both steps:
 The signal processing unit receives measured values from a volume flow sensor and/or from an airway pressure sensor and/or from an esophageal pressure sensor and/or from a volume sensor. The signal processing unit generates from these measured values the volume flow signal Vol' and/or the volume signal Vol and/or the pneumatic pressure signal $P_{aw}$ and/or $P_{es}$.

The signal processing unit receives measured values from a sensor array on the skin or in the body of the patient, especially from an EMG sensor or from an MMG sensor, or from an optical sensor, which operates in a contactless manner and is arranged at a spaced location from the patient. The signal processing unit generates the respiratory signal Sig from these measured values.

The signal processing unit carries out an initialization phase and a subsequent use phase. It generates a plurality of respective signal values in both phases.

During the initialization phase, the signal processing unit determines respective N values of the variable or of each variable that is/are correlated with respective N values of the variable or of each variable that is correlated with the pneumatic parameter $P_{mus}$ to be determined and occurs in the gradient model for N consecutive scanning times. The signal processing unit does not necessarily use the gradient model for this, since N consecutive values of the pneumatic parameter $P_{mus}$ to be determined or of another correlating variable are not necessarily available as yet during the initialization phase.

The term "scanning time" designates a time at which a signal in the lung-mechanical model or the pneumatic parameter $P_{mus}$ to be determined assumes or has assumed a certain value. The corresponding measurement and/or the calculation may have taken place at this time or at another time, especially at a later time.

The signal processing unit determines a value for the pneumatic parameter $P_{mus}$ for at least one scanning time during the use phase. The signal processing unit preferably determines a respective value for the pneumatic parameter $P_{mus}$ for a plurality of consecutive scanning times. In order to determine a value for the pneumatic parameter $P_{mus}$, which refers to a scanning time, the signal processing unit uses at least generated signal values for this scanning time,
the preset lung-mechanical model,
respective N values of the variable or each variable that occurs in the preset gradient model and is correlated with the pneumatic parameter $P_{mus}$, for N previous scanning times, wherein these N values were already determined during the initialization phase or during a use phase during a past time period, and
the preset gradient model.

The process according to the present invention and the signal processing unit according to the present invention provide a pneumatic parameter for the spontaneous breathing of the patient. This pneumatic parameter can be used to monitor a patient and to detect whether the patient is at risk. Furthermore, the parameter determined can be used to automatically synchronize the mechanical ventilation by a ventilator, which is connected to the patient, with the spontaneous breathing of the patient, especially to synchronize the ventilation strokes in terms of frequency and amplitude with the spontaneous breathing.

The lung-mechanical model used according to the present invention describes at least one relationship between the pneumatic parameter $P_{mus}$ to be determined and at least one signal for a scanning time. The values of the signals occurring in the lung-mechanical model consequently refer to the same scanning time. The signal processing unit generates the signal or each signal that occurs in the lung-mechanical model, preferably from measured values that are supplied by sensors, which are positioned at or in the vicinity of the patient or in the ventilator or in a fluid connection from the ventilator to the patient.

The gradient model can be used to describe and then automatically to use prior knowledge on how the pneumatic parameter $P_{mus}$ to be determined can change in the course of time. As a rule, the pneumatic parameter $P_{mus}$ does not change abruptly, but gradually and based on a, for example, anthropological natural law, which can be approximately depicted in the gradient model. The gradient model also makes it possible to describe the relationship of the pneumatic parameter $P_{mus}$ with a plurality of values of at least one other variable varying over time, which values are in the past, wherein this other variable is correlated with the pneumatic parameter $P_{mus}$. It is possible that the gradient model additionally takes into account and describes the at least one external variable at the scanning time.

The process according to the present invention and the signal processing unit according to the present invention make it possible to use the lung-mechanical model and the gradient model combined with one another. In many cases, the present invention eliminates the need to determine when the patient is inhaling spontaneously and when the patient is spontaneously exhaling again. This determination is subject, as a rule, to an uncertainty and to errors. It is rather possible in many cases to set up a lung-mechanical model and/or a gradient model, which are valid for both the inhalation (inspiration) as well as for the exhalation (expiration) of the patient.

A number N is preset according to the present invention and the gradient model specifies a value of the pneumatic parameter as a function of N chronologically earlier values. This number N may be equal to 1 or else greater than or equal to 2.

As a rule, the lung-mechanical model and the gradient model are valid only approximately. The deviation between the model and reality leads to a process noise. The process according to the present invention and the signal processing unit according to the present invention reduce the influence of this process noise compared to other approaches. In many cases, the process noise is "done away by averaging" to a certain extent. This happens especially because two models are used rather than only one.

In one embodiment, the gradient model describes a value for the pneumatic parameter $P_{mus}$ at least as a function of N earlier values for the pneumatic parameter $P_{mus}$. In another embodiment, the gradient model describes a value for the pneumatic parameter $P_{mus}$ at least as a function of N values of a variable correlating with the pneumatic parameter $P_{mus}$ at N earlier scanning times. These N values of the correlating variable are calculated in this case, and the value sought for the pneumatic parameter $P_{mus}$ is calculated with the use of these N values.

The preset gradient model describes according to the present invention a value of the pneumatic parameter $P_{mus}$ at least as a function of N values of a variable, which is variable over time and which is correlated with the pneumatic parameter $P_{mus}$, for example, of $P_{mus}$ itself. It is possible that the gradient model describes a value of the pneumatic parameter $P_{mus}$ as a function of a plurality of variables, which are variable over time and are correlated with the pneumatic parameter $P_{mus}$. The gradient model contains for at least one correlating variable N values for N consecutive scanning times. It is possible that the gradient model comprises N respective values for N consecutive scanning times for a plurality of correlating scanning times. It is also possible that even though the gradient model refers to a plurality of correlating variables, it refers to N respective values for N consecutive scanning times only for a single variable or for some of these variables. The gradient model refers to N values for at least one correlating variable and optionally to fewer than N different values, for example, only to one value for a scanning time, especially for the same scanning time to which the value of the pneumatic parameter $P_{mus}$ to be determined refers for at least one additional correlating variable.

A plurality of embodiments with a respective Kalman filter each will be described below. A Kalman filter comprises in the linear case a state equation, which connects a state vector by means of a transfer matrix at a scanning time with a state vector to a previous time, as well as a measuring equation (observation equation) with an observation matrix, wherein the state vector also occurs in the measuring equation.

In one embodiment of the present invention, the signal processing unit uses a preset first Kalman filter, which comprises the gradient model. This first Kalman filter has a first state vector, which refers to the variable correlated with $P_{mus}$. Preset is a function, which describes the pneumatic parameter $P_{mus}$ being sought as a function of the first state vector. In one embodiment, a sequence of N determined values of the pneumatic parameter $P_{mus}$ is used for N consecutive scanning times as a component of this first state vector.

In another embodiment, the signal processing unit uses a preset second Kalman filter, which comprises the lung-mechanical model. This second Kalman filter has a second state vector and a second observation equation. A value for the pneumatic parameter $P_{mus}$ forms a component of this second state vector. Values for the volume flow signal Vol' and/or for the volume signal Vol and/or for the pressure signal $P_{aw}$ or $P_{es}$ and/or for the respiratory signal Sig form components of an observation equation, forming components of an observation matrix in the linear case. All values in the second state vector preferably refer to the same scanning time.

These two embodiments with the two Kalman filters may be combined, preferably as follows: A third preset Kalman filter comprises both the gradient model and the lung-mechanical model. This third Kalman filter has a third state vector. This third state vector comprises the following components:
the state vector, which embodies the gradient model, for example, a sequence of N values of the pneumatic parameter $P_{mus}$ for N consecutive scanning times and optionally a combination of the first state vector and of the second state vector.

The observation equation of the third Kalman filter comprises, in turn, values for the volume flow signal Vol' and/or for the volume signal Vol and/or for the pressure signal $P_{aw}$, $P_{es}$ and/or for the respiratory signal Sig.

The use of a Kalman filter makes it possible to rapidly implement the signal processing unit. Different software programs for implementing Kalman filters are commercially available.

In one embodiment, the state equation of such a Kalman filter has the following form:

$$\underline{x}(k+1)=f[\underline{x}(k)]+\varepsilon_P$$

with a preset function f, wherein $\underline{x}(k)$ is the value of the state vector at the scanning time k and $\underline{x}(k+1)$ is the value of the state vector at the scanning time k+1. A part of this state vector is a value for the pneumatic parameter $P_{mus}$ for the scanning time k. In one embodiment, the third state vector comprises a value of the pneumatic parameter $P_{mus}$ for at least one earlier scanning time. The summand $\varepsilon_P$ describes the process noise, i.e., the deviation between the model and reality, and is preferably treated as a normally distributed random variable with the expected value zero.

In one variant, the state equation of the Kalman filter has the following form:

$$\underline{x}(k+1)=f[\underline{x}(k)]+g[u(k)]+\varepsilon_P(k)$$

with a preset function g, wherein the summand g[u] describes the influence of a variable u that is not dependent on the pneumatic parameter $P_{mus}$, for example, a relationship between the airway pressure, the lung volume and/or the heart rate and the respiratory rate of the patient.

In one embodiment, the two functions f and g are linear. A classical Kalman filter is preferably used in this case. If at least one function is nonlinear, an expansion of the classic Kalman filter for nonlinear systems can be used. Examples of such expansions are
Extended Kalman Filter (EKF),
Unscented Kalman Filter (UKF),
Sigma Point Filter (SPF), and
Particle Filter (PF).

In one embodiment, the lung-mechanical model comprises at least two relationships, namely,
a first relationship between the pneumatic parameter $P_{mus}$ as well as the volume flow signal Vol' and/or the volume signal Vol and/or the pressure signal $P_{aw}$, $P_{es}$, and
a second relationship between the pneumatic parameter $P_{mus}$ and the respiratory signal Sig.

For example, the signals of the first relationship are measured with pneumatic sensors, and the signals of the second relationship are measured with at least one electrical sensor, especially an EMG sensor.

The two relationships ideally always yield the same value for the pneumatic parameter $P_{mus}$. As a rule, these two relationships lead, by contrast, especially because of the process noise and often also because of the measurement noise, to two different values for the pneumatic parameter $P_{mus}$, which refer to the same scanning time. In one embodiment, the signal processing unit determines a first value and a second value for the pneumatic parameter $P_{mus}$ during the use phase for N scanning times. To determine a first value, the signal processing unit uses the first relationship as well as at least one value each of the volume flow signal Vol' and/or of the volume signal Vol and/or of the pressure signal $P_{aw}$ and/or $P_{es}$. To determine a second value, the signal processing unit uses the second relationship as well as at least one value of the respiratory signal Sig.

To determine a value of the pneumatic parameter $P_{mus}$ for a scanning time, the signal processing unit uses the N first values thus determined and N second values as well as the preset gradient model.

This embodiment makes it possible in an especially simple manner to use both relationships of the lung-mechanical model simultaneously. This embodiment avoids in many cases the necessity to combine the two values for a scanning time by preset weighting factors into one value. If weighting factors are used, the result often depends on the correct selection of the weighting factors, and it is often difficult to make the correct selection.

In a variant of this embodiment, a Kalman filter is used with a state equation and with an observation equation, wherein the state vector of the Kalman filter comprises as components values for the pneumatic parameter $P_{mus}$ at different scanning times and its observation equation comprises at least one first value and at least one second value of the pneumatic parameter $P_{mus}$ for the same scanning time, wherein the first value of the pneumatic parameter $P_{mus}$ is linked with the first relationship and the second value is linked with the second relationship of the lung-mechanical model, for example, it occurs in the first relationship and in the second relationship, respectively. The Kalman filter combines in itself two different relationships of the lung-mechanical model, for example, a relationship with electrically measured variables and a relationship with pneumatically measured variables. These two relationships ideally yield the same values for the pneumatic parameter $P_{mus}$. In practice, they yield, as a rule, different values, which are combined by the second Kalman filter into one value per scanning time of the pneumatic parameter without weighting factors being necessary. More than two relationships of the lung-mechanical model are also possible, which leads to a correspondingly larger observation equation.

The gradient model and the lung-mechanical model are used simultaneously and parallel according to the present invention. It is, however, possible that no value is available at a scanning time for a signal to which the lung-mechanical model refers or that a measured value lacks sufficient reliability. For example, a sensor does not yield a sufficiently reliable value or fails. Or else, the scanning time is in the future, and a value for the pneumatic parameter $P_{mus}$ shall be predicted.

In some cases, the lung-mechanical model still yields a sufficiently reliable value for the pneumatic parameter $P_{mus}$ despite the lack of a signal value. The lung-mechanical model and the gradient model preferably continue to be used simultaneously in this case. In other cases, the lung-mechanical model is not capable of providing a sufficiently reliable value for the pneumatic parameter $P_{mus}$ any longer in the absence of a signal value. If a value for the pneumatic parameter $P_{mus}$ shall be predicted, it is not necessary, and in many cases not possible, to predict values for the signals of the lung-mechanical model. It is, however, nevertheless possible in many cases to make a determination or a prediction with sufficient reliability only by means of the gradient model, at least over a limited time period. Only the gradient model is used for such a scanning time in order to determine the value of the pneumatic parameter $P_{mus}$ for this scanning time. If all needed values are available for the signals of the lung-mechanical model for a later scanning time, the gradient model and the lung-mechanical model will again be used simultaneously.

In one application, the time period, which is bridged over by abandoning the lung-mechanical model, which cannot be applied at times, as well as the prediction time period, for which future values of the pneumatic parameter $P_{mus}$ are predicted, comprises fewer than N scanning times, so that at least one set of measured signal values will affect this determined value of the pneumatic parameter $P_{mus}$, even if only the gradient model is used for the current scanning time. It is, however, also possible that the time period to be bridged over comprises N or even more than N scanning times.

In one embodiment, the lung-mechanical model comprises at least one model parameter, which is, as a rule, variable over time. The signal processing unit estimates for the model parameter or for each model parameter a respective value during the use phase and optionally also during the initialization phase and uses for this estimation the lung-mechanical model as well as signal values for the current scanning time and signal values for at least one earlier scanning time, preferably for a plurality of earlier scanning times. For example, the signal processing unit carries out a regression analysis ("fitting") in order to adapt the model parameters as best as possible to the signal values. A model parameter may have a physical, especially lung-mechanical, meaning. However, the approximately calculated model parameter values do not necessarily come close to a real physical value. The goal of the process according to the present invention is to determine the pneumatic parameter $P_{mus}$ rather than primarily to estimate lung-mechanical or other physical parameters.

According to the present invention, the signal processing unit determines during the initialization phase N values of the variable, which is correlated with the pneumatic parameter $P_{mus}$, for N consecutive scanning times. These N values are preset in one embodiment. In another embodiment, the N values for $P_{mus}$ or the variable correlated with $P_{mus}$ can be determined during the initialization phase without using the lung-mechanical model, for example, because the pneumatic parameter $P_{mus}$ or the other correlating variable can be measured directly during the initialization phase. In another embodiment, the N values of the pneumatic parameter $P_{mus}$ are determined during the initialization phase, and generated signal values as well as the lung-mechanical model are used for this purpose.

According to the present invention, the signal processing unit uses two computer-analyzable models. It is possible that these models are components of a source program, wherein an executable program is generated from the source program by compilation or by assembling or in another suitable manner and wherein the signal processing unit then executes this program during the use phase and preferably also during the initialization phase The present invention will be described below on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
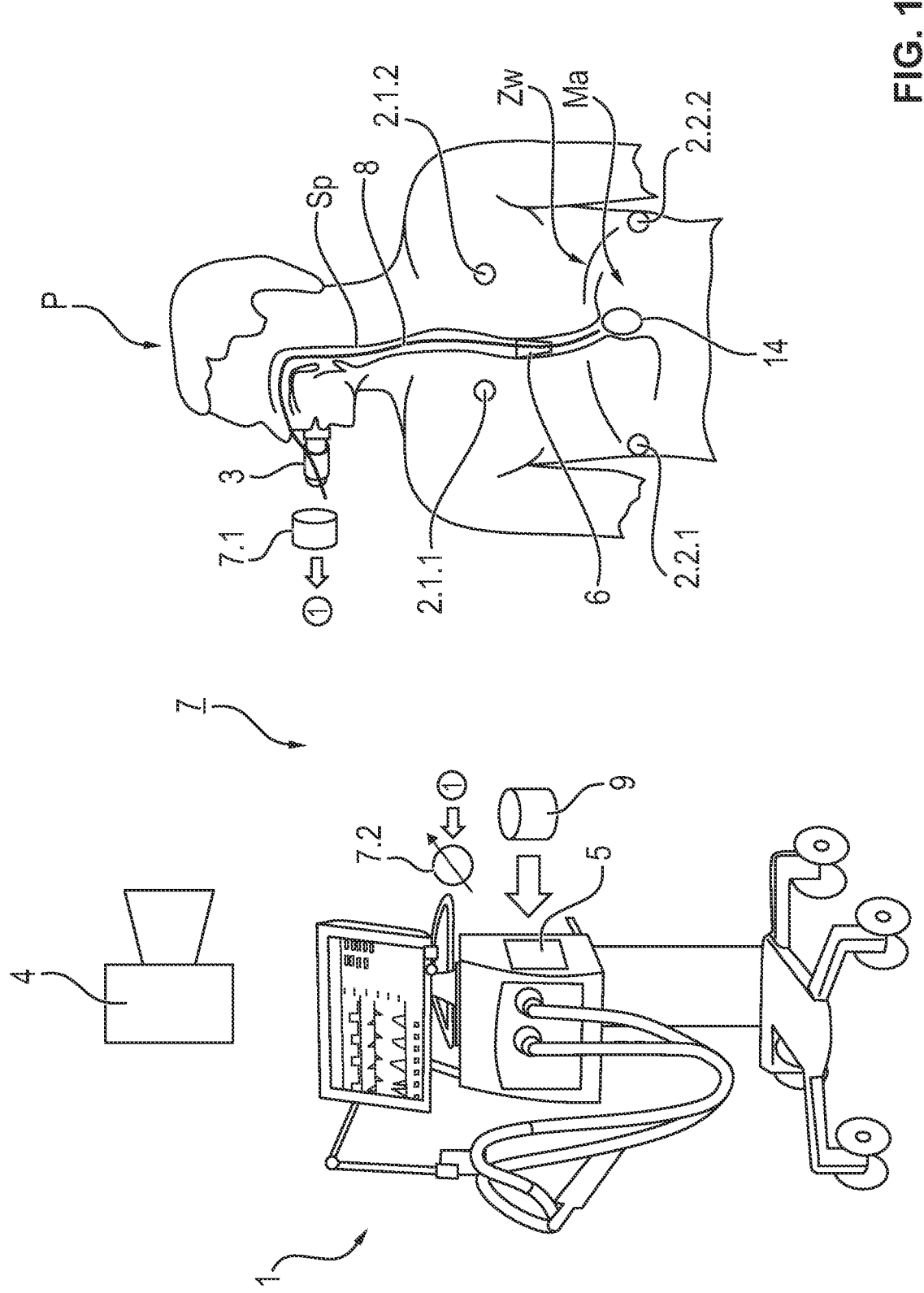
FIG. 1 is a schematic view showing which sensors measure which different variables for determining the pneumatic parameter $P_{mus}$.

Referring to the drawings, the present invention is used in the exemplary embodiment to determine a pneumatic parameter $P_{mus}$, which is correlated with the spontaneous breathing (intrinsic breathing activity) of a patient P. This pneumatic parameter $P_{mus}$ is variable over time, i.e., $P_{mus}=P_{mus}(t)$. This patient P is ventilated mechanically by means of a ventilator 1 at least from time to time, as a result of which a fluid connection is established from the ventilator 1 to the patient P, and this connection is a closed ventilation circuit between the ventilator 1 and the patient P in one embodiment. While the patient P is being ventilated mechanically, the mechanical ventilation, which is brought about by the ventilator, is superimposed to his spontaneous breathing, or the patient is fully sedated from time to time, i.e., he has no spontaneous breathing.

The knowledge of the pneumatic parameter $P_{mus}$ is preferably used to regulate the ventilator 1, for example, in order for the ventilator 1 to carry out ventilation strokes synchronously with the spontaneous breathing of the patient P. It is also possible to output the determined pneumatic parameter $P_{mus}$ continuously in a form perceptible by a human being and/or to generate and output alarms as a function of the pneumatic parameter $P_{mus}$. It is possible that the pneumatic parameter $P_{mus}$ determined is used both to synchronize the ventilation strokes of the ventilator 1 with the spontaneous breathing of the patient P and also to output the pneumatic parameter $P_{mus}$ in a form perceptible by a human being The pneumatic parameter $P_{mus}$ cannot be measured directly especially in case of mechanical ventilation. The pneumatic parameter $P_{mus}$, which is variable over time, is rather determined according to the present invention indirectly, and the values of a plurality of variables, which occur in the fluid connection from the ventilator 1 to the patient P, are used for the determination. These variables are called signals and the values of the variables are called signal values. A "signal" shall hereinafter be defined as the course in the time range or even in the frequency range of a directly or indirectly measurable variable, which is variable over time, and which is correlated with a physical variable. This physical variable is connected here with the spontaneous breathing and/or with the mechanical ventilation and/or with the cardiac activity of the patient P and is generated by at least one signal source in the body of the patient P and/or by the ventilator 1. A "respiratory signal" is correlated with the spontaneous breathing and/or with the mechanical ventilation of the patient P, and a "cardiogenic signal" is correlated with the cardiac activity of the patient P.

The measured values, which originate from sensors at or in the patient P or close to the patient P or in the fluid connection from the ventilator 1 to the patient P, are processed at each scanning time $t_i$. A set of signal values, which set comprises the values of different signals at this scanning time is generated thereby. Using at least one set of signal values, preferably a plurality of sets of signal values, the signal processing unit 5 determines an estimated value $P_{mus,est}(t_i)$ for the pneumatic parameter $P_{mus}$. The subscript est indicates that the determined signal values and the value for $P_{mus}$ are estimated and do, as a rule, deviate from the actual values.

FIG. 1 shows schematically which signals can be generated from measured values, for which the measured values are processed in a suitable manner. Shown are:
the patient P ventilated mechanically at least from time to time,
the esophagus Sp, the stomach Ma and the diaphragm Zw of the patient P,
a flexible connection piece 3, which is located in the mouth of the patient P during the ventilation,
a flexible measuring catheter 8, which is introduced into the esophagus Sp of the patient and which begins in the connection piece 3,
the ventilator 1, which ventilates the patient mechanically at least from time to time and comprises a data-processing signal processing unit 5, which has read access at least from time to time to a memory 9,
a sensor array with two sets 2.1.1 through 2.2.2 of sensors with at least two respective measuring electrodes each, wherein the measuring electrode sets 2.1.1 and 2.1.2 are arranged close to the sternum of the patient P and the measuring electrode set 2.2.1 and 2.2.2 are arranged close to the costal arch, and wherein the sensor array comprises, in addition, at least one reference electrode, not shown, for grounding,
a pneumatic sensor 7, which is located at a distance in space from the body of the patient P,
an optional sensor 4, which comprises an image recording device and an image analysis unit and is directed towards the thoracic region of the patient P,
an optional pneumatic sensor 6 in the form of a probe or of a balloon in the esophagus Sp and close to the diaphragm Zw of the patient P, wherein the sensor 6 measures a pressure $P_{es}$ (pressure in esophagus) in the esophagus Sp and is in fluid connection with the measuring catheter 8, and
an optional gastric probe 14 in the stomach Ma of the patient P, which is likewise in a fluid connection with the measuring catheter 8.

The pneumatic sensor 7 comprises a transducer 7.1 comprising an opening, which is arranged in the vicinity of the mouth of the patient P and taps air from the fluid connection. The tapped air is transmitted via a flexible tube (suggested by arrows) to a pressure sensor 7.2, which measures a parameter for the airway pressure $P_{aw}$ (pressure in airway) in the fluid connection and a parameter for the volume flow Vol'. In one embodiment, the transducer 2.1 is arranged in or at a Y-piece close to the connection piece 3, i.e., close to the mouth of the patient P. It is also possible that the pneumatic sensor 7 comprises two individual sensors, namely, a sensor for the airway pressure $P_{aw}$ and a sensor for the volume flow Vol'.

The measuring electrode sets 2.1.1 through 2.2.2 of measuring electrodes as well as the reference electrode, not shown, yield after signal processing an electrical respiratory signal Sig, which is correlated with the pneumatic parameter $P_{mus}$ to be determined. Instead of an electrical respiratory signal (EMG signal), it is also possible to generate and use a signal in the form of a mechanomyogram (MMG signal). As a rule, the EMG signal or the MMG signal is generated by a superimposition of a respiratory signal and of a cardiogenic signal. The signal processing unit 5 compensates the influence of the cardiogenic signal by calculation to the extent possible, for example, as described in DE 10 2015 015 296 A1 (corresponding US 2018344194 (A1) is incorporated herein by reference), in DE 10 2007 062 214 B3 (corresponding U.S. Pat. No. 8,109,269 (B2) is incorporated herein by reference) or in M. Ungureanu and W. M. Wolf: "Basic Aspects Concerning the Event-Synchronous Interference Canceller," IEEE Transactions on Biomedical Engineering, Vol. 53, No. 11 (2006), pp. 2240-2247 (which is incorporated herein by reference).

The pneumatic sensor 7 yields as the signal—after signal processing—the airway pressure $P_{aw}$ (pressure in airway) in front of the mouth of the patient P. As long as the patient P is being ventilated mechanically, this airway pressure $P_{aw}$ results from a superimposition of the spontaneous breathing of the patient P and the mechanical ventilation—or even from the mechanical ventilation only. The optional pneumatic sensor 6 yields as the signal—after signal processing—the pressure in the esophagus $P_{es}$ (pressure in esophagus), which likewise results from a superimposition of spontaneous breathing and mechanical ventilation. The optional gastric probe 14 measures the gastric pressure $P_{ga}$ in the stomach Ma of the patient P.

Different signals may also be used as the respiratory signal Sig or as a respiratory signal Sig. It is also possible to use two respiratory signals $Sig_1$ and $Sig_2$. In one embodiment the electrical signal from the measuring electrodes 2.1.1 through 2.2.2 on the skin of the patient P is used as the respiratory signal Sig or as a respiratory signal Sig. In another embodiment, a signals from the pneumatic sensor 6 and/or from the gastric probe 14 are used as the respiratory signal Sig or as a respiratory signal Sig.

In addition, the volume flow Vol' of breathing air into and out of the lungs of the patient P and/or the volume Vol of the lungs of the patient P can be derived as signals from the measured values of the pneumatic sensor 7, 14, of the optional pneumatic sensor 6 and/or of the optional optical sensor 4. It is possible to calculate the lung volume Vol by numerical integration over the measured volume flow Vol'. It is also possible to derive the lung volume Vol from measured values of the optical sensor 4, on the one hand, and to obtain it by numerical integration, on the other hand, and then to average in a suitable manner between the two signals determined in different ways.

A preset, computer-analyzable lung-mechanical model 20 and a preset, computer-analyzable gradient model 22 are stored in the memory 9, to which the signal processing unit 5 has read access at least from time to time. The signal processing unit 5 is capable of applying both models automatically to signal values. The lung-mechanical model 20 has at least one and preferably more model parameters, which are, as a rule, variable over time and for which the signal processing unit 5 calculates at least once a respective value each, preferably one value for a plurality of scanning times, in order to take changes over time into account.

Figure 2:
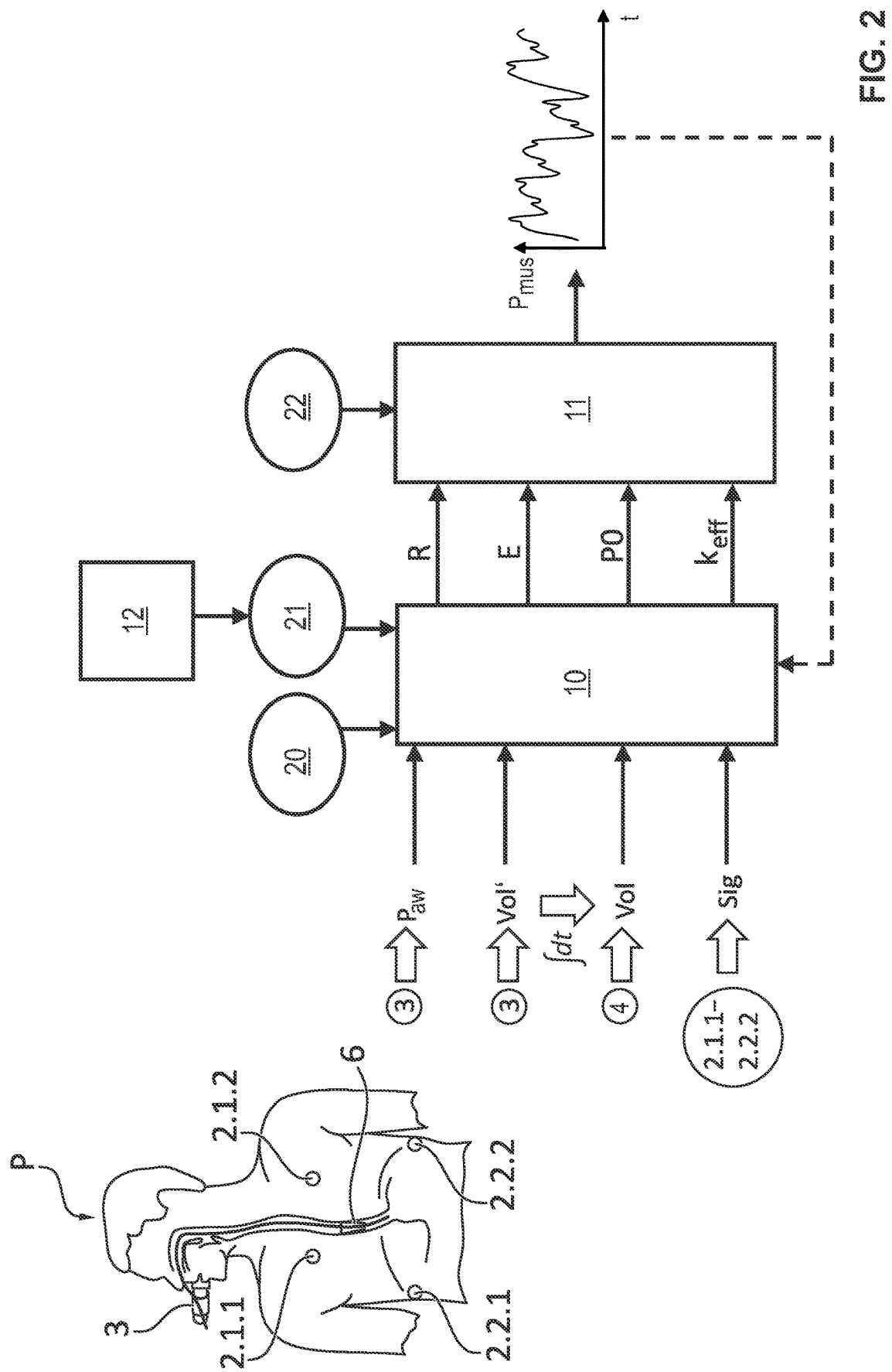
FIG. 2 is a schematic view showing how a parameter estimator interacts automatically with a $P_{mus}$ estimator.

FIG. 2 schematically shows the interaction of a parameter estimator 10 with a $P_{mus}$ estimator 11. Both the parameter estimator 10 and the $P_{mus}$ estimator 11 are implemented on the signal processing unit 5 and are preferably implemented by means of a software program. The parameter estimator 10 has read access to the preset lung-mechanical model 20 and optionally to computer-analyzable weightings 21 and it calculates values for the parameters of the lung-mechanical model 20, which are variable over time. A weighting estimator 12 has calculated these weightings 21, which will be described below. The weightings 21 may be variable over time. The $P_{mus}$ estimator 12 has read access to the preset gradient model 22 for $P_{mus}$ and receives the model parameter values, which the parameter estimator 11 has calculated. The $P_{mus}$ estimator 12 calculates estimated values $P_{mus,est}(t_i)$ for the pneumatic parameter $P_{mus}$ to be determined, which refer to scanning times L.

The signal processing unit 5 uses these values $P_{mus,est}(t_i)$ in one embodiment in order to actuate the ventilator 1, e.g., for a proportional control, i.e., the intensity of the mechanical ventilation, especially the pressure in the fluid connection to the patient P, which pressure is brought about by the ventilation strokes and is variable over time, is proportional to the determined current spontaneous breathing of the patient P and is preferably proportional to $P_{mus}$. In one embodiment, this estimated pneumatic parameter $P_{mus}$ is fed back again to the parameter estimator 10 in order to improve future estimations of $P_{mus}$.

Consequently, in the exemplary embodiment, the lung-mechanical model 20 is used, on the one hand, which comprises at least one relationship, preferably in the form of a model equation, between the pneumatic parameter $P_{mus}$ sought and a plurality of measurable signals, wherein the relationship or each relationship connects different signal values for the same scanning time. A measurable signal is defined as a variable, which is, as a rule, variable over time and which can be derived by signal processing from measured values of sensors, in this case, for example, from the sensors 4, 6, 7 and/or 14.

This lung-mechanical model 20 contains in the exemplary embodiment at least one model parameter and preferably more model parameters, wherein the model parameter or each model parameter is, as a rule, likewise variable over time. The lung-mechanical model is preferably linear in each model parameter, but it is not necessarily linear in the signals. The model parameters do, however, change their values more slowly than does the pneumatic parameter $P_{mus}$ to be determined. This lung-mechanical model 20 has, of course, only an approximate validity.

In one embodiment, the lung-mechanical model 20 comprises the model equation $$P_{aw}(t) = R * \text{Vol}'(t) + E * \text{Vol}(t) + P_{mus}(t) + P0 + \sigma 1_n. \quad (1)$$

This model equation (1) has three model parameters, namely, the two lung-mechanical factors R and E as well as the summand P0. The factor R (resistance) describes the breathing resistance, which the airways of the patient P offer against the volume flow of the air flowing into and out of the lungs. The factor E (elastance) describes the elasticity of the lungs. The summand P0 (pulmonary end-expiration pressure, PEEP) describes the effect of an incomplete exhalation by the patient P. The summand $\sigma 1_n$ results from the inevitable process noise (deviation between model and reality) and is preferably treated as a normally distributed random variable with the expected value zero. The estimated values for the model parameters are not necessarily good estimations for the values of the physical lung parameters, but they are used above all to estimate the pneumatic parameter $P_{mus}$.

It is also possible to use the following model equation:

$$P_{aw}(t) = R_1 * \text{Vol}'(t) + R_2 * \text{Vol}'(t) * |\text{Vol}'(t)| + E * \text{Vol}(t) + P_{mus}(t) + P0 + \sigma 1_n. \quad (2)$$

|x| designates the absolute value of x.
This equation can be rewritten as follows:

$$P_{aw}(t) = R(\text{Vol}') * \text{Vol}'(t) + E * \text{Vol}(t) + P_{mus}(t) + P0 + \sigma 1_n, \quad (3)$$

in which $R(\text{Vol}') = R_1 + R_2 * |\text{Vol}'(t)|$.

The model parameters can be estimated more rapidly in some cases with equation (3) than with equation (2).

In a variant, all model parameters R, E and P0 in the model equation (1) are assumed to be approximately constant over time. The model equation (1) is differentiated once according to time, as a result of which the summand P0 assumed to be constant disappears. This procedure leads to the following lung-mechanical model equation:

$$P_{aw}'(t) = R * \text{Vol}''(t) + E * \text{Vol}'(t) + P_{mus}' + \sigma 1_n'. \quad (4)$$

The corresponding procedure can be applied to the model equations (2) and (3).

It is also possible that the pressure $P_{es}$ in the esophagus Sp of the patient P is measured, doing so by means of the probe 6. This embodiment can replace the embodiment in which the airway pressure $P_{aw}$ is measured by means of the sensor 7. It is also possible that the sensor 7 measures the airway pressure $P_{aw}$ and the probe 6 also measures the pressure $P_{es}$ in the esophagus.

For example, the following lung-mechanical model equation is used in that case:

$$P_{es}(t) = E_{cw} * \text{Vol}(t) - P_{mus}(t) + P0 + \sigma 2_n \quad (5)$$

or also $$P_{es}'(t) = E_{cw} * \text{Vol}'(t) - P_{mus}'(t) + \sigma 2'_n \quad (6)$$

after the model equation (5) was differentiated according to time.

The lung-mechanical factor $E_{cw}$ describes the elasticity on the basis of the chest wall (chest wall) of the patient P. The preferably normally distributed summand $\sigma2_n$ describes, in turn, the process noise.

In another embodiment, a model equation with additional summands, for example, the following lung-mechanical model equation, is preset and used instead of the model equations (1) or (4):

$$P_{aw}(t)=R*\text{Vol}'(t)+E*\text{Vol}(t)+I*\text{Vol}''(t)+Q*(t)|\text{Vol}'(t)| \\ \quad |*\text{Vol}'(t)+S*\text{Vol}''(t)+P_{mus}(t)+P0+\sigma3_n. \quad (7)$$

Here, Q describes the resistance to the air flow, which the turbulent flow generates in a flexible tube from the ventilator 1 to the patient P and/or in the trachea of the patient P, S is the change in the compliance of the lungs and/or of the thorax as a function of the volume Vol of the lungs and I describes the resistance to the acceleration of the breathing air, this resistance I being negligibly low at a sufficiently low acceleration.

The pneumatic parameter $P_{mus}$ to be determined is correlated, in addition, with the electrical respiratory signal Sig, which was generated from measured values of the sensor array with the measuring electrodes 2.1.1 through 2.2.2, or with a respiratory MMG signal. This correlation is described in the simplest case by the following model equation, which likewise belongs to the lung-mechanical model 20:

$$P_{mus}(t)=k_{eff}*\text{Sig}(t)+\sigma4_n. \quad (8)$$

It is also possible that the respiratory signal Sig is generated by measured values from other sensors, for example, the probe 6 in the esophagus Sp or the gastric probe 14 in the stomach 14. Another model equation, which describes the relationship between $P_{mus}$ and Sig, is preferably used in this case.

The factor $k_{eff}$ describes the neuromuscular efficiency of the respiratory muscles of the patient P, i.e., how well the respiratory muscles convert the electrical signals generated in the body of the patient P into pneumatic breathing activity. This factor $k_{eff}$ is an additional model parameter and is, as a rule, likewise variable over time. The preferably normally distributed summand $\sigma4_n$ describes in turn the process noise.

A respiratory signal Sig is generated in the embodiment described so far. It is also possible that two different respiratory signals $Sig_1$ and $Sig_2$ are generated, preferably with the use of measured values of different sensors, these two signals $Sig_1$ and $Sig_2$ being both correlated with the spontaneous breathing of the patient P.

$$P_{mus}(t)=k_{eff.1}*\text{Sig}_1(t)+k_{eff.2}*\text{Sig}_2(t)+\sigma5_n \quad (9)$$

with two model parameters in the form of two factors $k_{eff.1}$ and $k_{eff.2}$.

At least one of the model equations (1) through (7) as well as the model equation (8) or (9) form together a lung-mechanical model 20 of the exemplary embodiment which is stored in the memory 9. Each model equation of the lung-mechanical model 20 describes at least one relationship between the pneumatic parameter $P_{mus}$ to be determined and a plurality of measurable signals and is true for a respective scanning time t each. Because of the measurement noise (measured values are subject to errors) and of the process noise (the model is true only approximately), a plurality of model equations are used, even if this leads to a redundancy.

In addition to the lung-mechanical model 20, a model 22 for the time curve of the pneumatic parameter $P_{mus}$ is used over a plurality of scanning times. Here, N is a preset number, which is preferably greater than or equal to 2.

A preferred gradient model 22 for $P_{mus}$ comprises a state space model (state space model, process function) of the $N^{th}$ degree, i.e., a model of the form of $$\underline{x}(t_k)=A*\underline{x}(t_{k-1})+B*u(t_k)+\underline{\varepsilon}P(t_k). \quad (10)$$

Here, $t_k$ designates a vector with N scanning times, $\underline{x}(t_k)$ designates a state vector with N components per occurring variable for the N different scanning times of $t_k$, $u(t_k)$ designates an external input signal, e.g., a measured heart rate or a concentration of breathing gases, for example $O_2$ and/or $CO_2$, or of an anesthetic gas, and $\underline{\varepsilon}_P(t_k)$ designates the process noise, each doing so at the current scanning time $t_k$. The value $P_{mus}(t_k)$ to be determined for the pneumatic parameter $P_{mus}$ is a function of the state vector $\underline{x}(t_k)$, wherein this function is also called observation model (observation function) and comprises the following observation equation:

$$P_{mus}(t_k)=g[\underline{x}(t_k)]. \quad (11)$$

One embodiment of this gradient model 22 comprises an autoregressive model of the $N^{th}$ order, i.e., $$P_{mus}(t_k)=a_1*P_{mus}(t_{k-1})+a_2*P_{mus}(t_{k-2})+ \ldots +a_N*P_{mus} \\ (t_{k-N})+\varepsilon_P(t_k). \quad (12)$$

Here, N is the number preset for the gradient model 22. The factors $a_1, a_2, \ldots, a_N$ for the N previous values of $P_{mus}$ are preferably preset, for example, on the basis of a determination in a training phase prior to the use, but they may also be unknown and yet to be determined. The individual scanning times are designated by $t_k, t_{k-1}, t_{k-N}$. The summand $\varepsilon_P(t_k)$ describes the process noise and is preferably likewise treated as a normally distributed random variable with the expected value zero. The normally distributed random variables $\sigma1_n, \sigma2_n, \sigma3_n, \sigma4_n$ and $\varepsilon_P$ may have different variances.

The state vector has the form $\underline{x}(t_k)=[P_{mus}(t_k), P_{mus}(t_{k-1}), \ldots, P_{mus}(t_{k-N})]$ in this embodiment. The function (11) (observation equation) has the form $P_{mus}(t_k)=\underline{x}_1(t_k)$.

For example, it is assumed in the gradient model 22 that the pneumatic parameter $P_{mus}$ changes so slowly that the second derivation is negligibly small after time. The following gradient model with N=2 results from this:

$$P_{mus}(t_k)=P_{mus}(t_{k-1})+[P_{mus}(t_{k-1})-P_{mus}(t_{k-2})]+ \\ \varepsilon_P=2*P_{mus}(t_{k-1})-P_{mus}(t_{k-2})+\varepsilon_P. \quad (13)$$

It is also possible to use an autoregressive gradient model with, e.g., N=2 and to estimate the two factors a1 and a2 in advance by means of a random sample and to set them thereby in advance. N may, of course, also be greater than or equal to 3.

It is also possible to estimate the N parameters $a_1, a_2, \ldots, a_N$ of the autoregressive model (12) at the operating time. One possibility of estimating these parameters is the following: The state vector $\underline{x}(t_k)$ is expanded by the N unknown parameters. By calculating the expanded state vector, estimated values are determined for the N unknown parameters. A time curve model, for example, a "random walk," is preferably preset for the unknown parameters. Even if the gradient model 22 with the state vector $\underline{x}(t_k)$ was linear, the gradient model expanded by the N parameters is not, as a rule, linear. A nonlinear Kalman filter is used for the estimation.

Breathing is a periodic process. The pneumatic parameter $P_{mus}$ being sought also changes therefore approximately periodically with a frequency that is, as a rule, variable over time. An oscillator model is used therefore as the gradient model 22 in one embodiment. The oscillator model may be, for example, a model of a damped harmonic oscillator, which [model] is discretized in time. In one embodiment, the phase and the amplitude of the spontaneous breathing, more precisely, the respective values at N respective scanning times of a breath, are at least two state variables of the state space model, which are correlated with the pneumatic parameter $P_{mus}$ being sought. Additional state variables of the state vector are, for example, estimated values of the pneumatic parameter $P_{mus}$ for previous scanning times.

In a different embodiment, the course of the pneumatic parameter $P_{mus}$ within a breath is described as a weighted sum of a plurality of Gaussian bell curves (augmented Gaussian kernel). Each Gaussian bell curve is described by its respective height, its respective width and its respective position in time within the breath. These three variables, which are variable over time, form three state variables of the state space model, which are correlated with the pneumatic parameter $P_{mus}$ being sought. These are 3*M state variables in the case of M Gaussian bell curves. The weighting factors are either preset or are model parameters, whose values are estimated.

It is also possible to preset and use a Gaussian process prior as the gradient model 22. Smooth, periodic or quasi-periodic signals can be modeled by means of a Gaussian process prior. The use of a Gaussian process prior makes it possible to introduce different hypotheses on $P_{mus}$ into the gradient model 22. A model for a Gaussian process is capable of depicting a plurality of different signal curves and can be readily adapted to different patients with different breathing efforts. Such a Gaussian process prior is described in Hartikainen, J. and Särkkä, S.: "Kalman filtering and smoothing solutions to temporal Gaussian process regression models," in: *Proceedings of IEEE International Workshop on Machine Learning for Signal Processing (MLSP)*, 2010, which is incorporated herein by reference. It is possible to transform a Gaussian process prior into the form of a state space model and then to insert it directly into the gradient model 22. Since the Gaussian process prior is integrated into the state space model, it is not necessary, unlike in classical Gaussian processes, to invert large matrices.

In one embodiment, the gradient model 22 comprises an input signal $u(t_k)$. Thanks to this input signal $u(t_k)$, the influence of external variables on the course of the pneumatic parameter P, for example, the influence of the airway pressure, of the lung volume, of the concentration of breathing gas or of the current heart rate of the patient, can be taken into account. The interaction between the patient P and a ventilator 1 can be readily taken into account in the gradient model 22 in this manner. This leads to more accurate predictions.

The signal processing unit 5 carries out an initialization phase and a subsequent use phase. The signal processing unit 5 preferably applies the lung-mechanical model 20 in both phases, whereas it uses the gradient model 22 in the use phase only.

The initialization phase comprises at least N scanning times, N being precisely the number preset for the gradient model 22. The signal processing unit 5 determines a respective value $P_{mus,est}(t_i)$ for the pneumatic parameter $P_{mus}$ for these at least N scanning times $t_1, t_2, \ldots, t_N$ during the initialization phase. The signal processing unit 5 preferably uses for this purpose the lung-mechanical model 20 as well as values of generated signals for the N scanning times $t_1, t_2, \ldots, t_N$. In another embodiment, an occlusion, during which the mechanical ventilation of the patient P is stopped for a short time period and the pneumatic parameter $P_{mus}$ can be measured directly, is carried out during the initialization phase. It is also possible that N values are available for the pneumatic parameter $P_{mus}$ from earlier determinations and are used or are preset in another manner.

During the use phase, the signal processing unit 5 uses the gradient model 22 as well as the N previous values $P_{mus,est}(t_{i-N}), \ldots, P_{mus,est}(t_{i-1})$, and, in addition, the lung-mechanical model 20 and signal values Vol'$(t_i)$, Vol$(t_i)$, Sig$(t_i)$ in order to calculate an estimated value $P_{mus,est}(t)$ for the current scanning time $t_i$.

In one embodiment, the pneumatic parameter $P_{mus}$ is determined by means of a Kalman filter. In one embodiment of the exemplary embodiment, the Kalman filter describes a system, here the system with ventilator 1 and the respiratory system of the patient P, by means of a state space equation and of an observation equation. The state space equation results from the gradient model 22, and the observation equation [results] from the lung-mechanical model 20. In agreement with the usual notation, the abbreviating notation (k) is used instead of $(t_k)$.

The gradient model 22 and the lung-mechanical model 20 are used simultaneously according to the present invention in order to determine the value of the pneumatic parameter $P_{mus}$ for a scanning time. In one embodiment, the gradient model 22 is implemented by means of a Kalman filter, the Kalman filter comprising for the gradient model 22 a state space model in the form of a state space equation $$\underline{x}(t_k)=\underline{f}[\underline{x}(t_{k-1})]-u(t_k)+\varepsilon_P(t_k) \tag{14}$$

and an observation equation $$P_{mus}(t_k)=g[x(t_k)]. \tag{15}$$

The summand $u(t_k)$ takes into account the influence of measurable external factors at the N scanning times $t_k$ on the system described and hence on the pneumatic parameter $P_{mus}$.

The lung-mechanical model 20 is introduced via an additional observation equation.

In one embodiment, the additional observation equation is obtained from the lung-mechanical model equations (1) and (8), where equation (8) is rearranged into:

$$Sig(t)=1/k_{eff}*P_{mus}(t)+\sigma 5_n \tag{16}$$

with another summand $\sigma 5_n$ for the process noise, which is preferably likewise a normally distributed random variable with the expected value zero.

The state space equation will now be:

$$\underline{x}(k+1) = \underline{F}(k)*\underline{x}(k) + \varepsilon_P \tag{17}$$

with $$\underline{x}(k) = \begin{pmatrix} P_{mus,est}(k-1) \\ P_{mus,est}(k-2) \\ \ldots \\ P_{mus,est}(k-N) \end{pmatrix} \tag{18}$$

$$\underline{F}(k) = \begin{pmatrix} a_1 & a_2 & \ldots & a_N \\ 1 & 0 & \ldots & 0 \\ \ldots & & & \\ 0 & 0 & & 1 \end{pmatrix} \tag{19}$$

and $$\underline{\varepsilon}_p = \begin{pmatrix} \varepsilon_p \\ 0 \\ \ldots \\ 0 \end{pmatrix}. \tag{20}$$

The observation equation is $$\underline{c}(k) = \underline{B}(k) + \underline{H}(k) * \underline{x}(k) + \underline{\sigma}_n \text{ with} \tag{21}$$

$$\underline{c}(k) = \begin{pmatrix} P_{aw}(k) \\ Sig(k) \end{pmatrix} \tag{22}$$

$$\underline{B}(k) = \begin{pmatrix} R*Vol'(k)+E*Vol(k)+P0 \\ 0 \quad 0 \quad 0 \end{pmatrix} \tag{23}$$

$$\underline{H}(k) = \begin{pmatrix} 1 & 0 & \ldots & 0 \\ 1/k_{\text{eff}} & 0 & \ldots & 0 \end{pmatrix} \tag{24}$$

$$\underline{\sigma}_n = \begin{pmatrix} \sigma 1_n \\ \sigma 3_n \end{pmatrix}. \tag{25}$$

The state space vector $\underline{x}(k)$ is specified, in turn, by the equation (18).

This embodiment has especially the following advantages:

It is not necessary to detect individual breaths of the patient P or individual phases phases, especially inhalation and exhalation, during the breaths of the patient P and to adapt model parameters or other parameters of a model being used to the duration or the intensity of individual breaths. The measured values are rather obtained and processed uniformly and at a preset scanning frequency, i.e., independently from the breathing and from the ventilation.

The lung-mechanical model 20 used contains two model equations (1) and (8). The model equation (1) describes a relationship between the pneumatic parameter $P_{mus}$ and a plurality of measurable pneumatic signals. The model equation (8) describes a relationship between the same pneumatic parameter $P_{mus}$ and a measurable electrical respiratory signal Sig. The separate application of these two equations (1) and (8) leads, as a rule, to different estimations for the pneumatic parameter $P_{mus}$, namely, to a pneumatically determined estimation $P_{mus,pneu}(t_i)$ and to an electrically determined estimation parameter $P_{mus,EMG}(t_i)$ and $P_{mus,MMG}(t_i)$ for the pneumatic parameter $P_{mus}$. Both estimations refer to the same scanning time Thanks to the Kalman filter, an averaging is performed via these two estimations $P_{mus,pneu}$ and $P_{mus,EMG}$, without weightings having to be preset for this averaging.

The optional weightings 21 for the measured signals can be introduced without having to change the gradient model 22, namely, into the observation matrix B(k) of the observation equation (21).

Standard programs, with which a Kalman filter can be rapidly implemented, are available commercially.

Both models 22 and 20 are used simultaneously according to the present invention, e.g., as described by the equations (17) through (20) as well as (21) through (25). It is possible that no values at all or no sufficiently reliably measured values, e.g., no values for Vol($t_x$), for Vol'($t_x$), for $P_{aw}(t_x)$, for $P_{aw}(t_x)$ or for Sig($t_x$), are available for an individual scanning time $t_x$ for at least one signal of the lung-mechanical model 20. Only the gradient model 22 is used in one embodiment for such a scanning time $t_x$.

It is also possible to use a separate parameter estimator 10 in order to estimate the values of the model parameters in a lung-mechanical model 20, in order to estimate them continuously. Individual breaths or the inhalation and the exhalation need not be detected and be distinguished from one another in this variant, either.

The values of the model parameters are estimated from sets of signal values, with a plurality of sets of signal values being preferably used for a plurality of consecutive scanning times in order to estimate a set of model parameter values.

The parameter estimator 10 preferably uses a statistical method to estimate the set of model parameter values. In one embodiment, a recursive method is used to estimate the parameter values. An updated model parameter value is estimated here using the previous model parameter values, the current signal value set and optionally at least one previous signal value set. In one embodiment, the parameter estimator 10 uses at least one of the methods Gradient-based Maximum Likelihood Estimation,
Expectation Maximization,
Variational Inference,
Markov-Chain-Monte-Carlo,
Ordinary Least Squares,
Recursive Least Squares.

It is also possible to use a separate Kalman filter for the parameter estimator 10. This Kalman filter uses, for example, the state space equation $$\underline{x}(k) = \underline{I}*\underline{x}(k-1)+\underline{\varepsilon}(\text{"Random Walk"}), \tag{26}$$

in which $$\underline{x}(k) = \begin{pmatrix} R(k) \\ E(k) \\ P0(k) \\ k_{\text{eff}}(k) \end{pmatrix} \tag{27}$$

$$\underline{I} = \begin{pmatrix} 1 & 0 & 0 & 0 \\ 0 & 1 & 0 & 0 \\ 0 & 0 & 1 & 0 \\ 0 & 0 & 0 & 1 \end{pmatrix} \tag{28}$$

and wherein $$\underline{\varepsilon} = \begin{pmatrix} \varepsilon 1 \\ \varepsilon 2 \\ \varepsilon 3 \\ \varepsilon 4 \end{pmatrix} \tag{29}$$

describes the respective error during the estimation of the four model parameter values R, E, P0, $k_{\text{eff}}$. The model parameters are consequently variable over time. The observation equation is, for example, $$P_{aw}(k) = s(k)*\underline{x}(k)+v, \tag{30}$$

wherein $$s(k) = (\text{Vol'}(k), \text{Vol}(k), \text{Sig}(k), 1) \tag{31}$$

and wherein v is, in turn, treated as a normally distributed random variable with the expected value 0.

It is possible to use a plurality of model parameters $R_1$, $R_2$ for the resistance, for example, a model parameter $R_1$ for a linear dependence of the resistive pressure drop on the volume flow and another model parameter $R_2$ for a square or other dependence of the resistive parameter $R_2$ on the volume flow Vol', for example, the model equation (2). All model parameters $R_1$, $R_2$ are variable over time. The model parameter $k_{\text{eff}}$ for the neuromuscular efficiency may contain a plurality of individual model parameters $k_{\text{eff},1}$, $k_{\text{eff},2}$, . . . as well, for example, for different sets of measuring electrodes, which are attached at different locations on the skin of the patient P and/or measure electrical signals in a different way.

In one variant, the state space equation $$\underline{x}(k) = \underline{I} * \underline{x}(k-1) + \underline{\varepsilon}, \quad (32)$$

in which $$\underline{x}(k) = \begin{pmatrix} P_{mus,est}(k) \\ R(k) \\ E(k) \\ Po(k) \\ k_{eff}(k) \end{pmatrix} \quad (33)$$

as well as the observation equation $$\underline{c1}(k) = B(k) * \underline{x}(k) + \underline{err}(k), \quad (34)$$

in which $$\underline{c1}(k) = \begin{pmatrix} P_{aw}(k) \\ 0 \end{pmatrix} \quad (35)$$

$$\underline{B1}(k) = \begin{pmatrix} 1 & -Vol'(k) & -Vol(k) & 0 & -1 \\ 1 & 0 & 0 & Sig(k) & 0 \end{pmatrix} \quad (36)$$

$$\underline{err}(k) = \begin{pmatrix} \varepsilon(k) \\ \zeta(k) \end{pmatrix} \quad (37)$$

are used, wherein ε is the process noise and ζ is the measurement noise.

Figure 3:
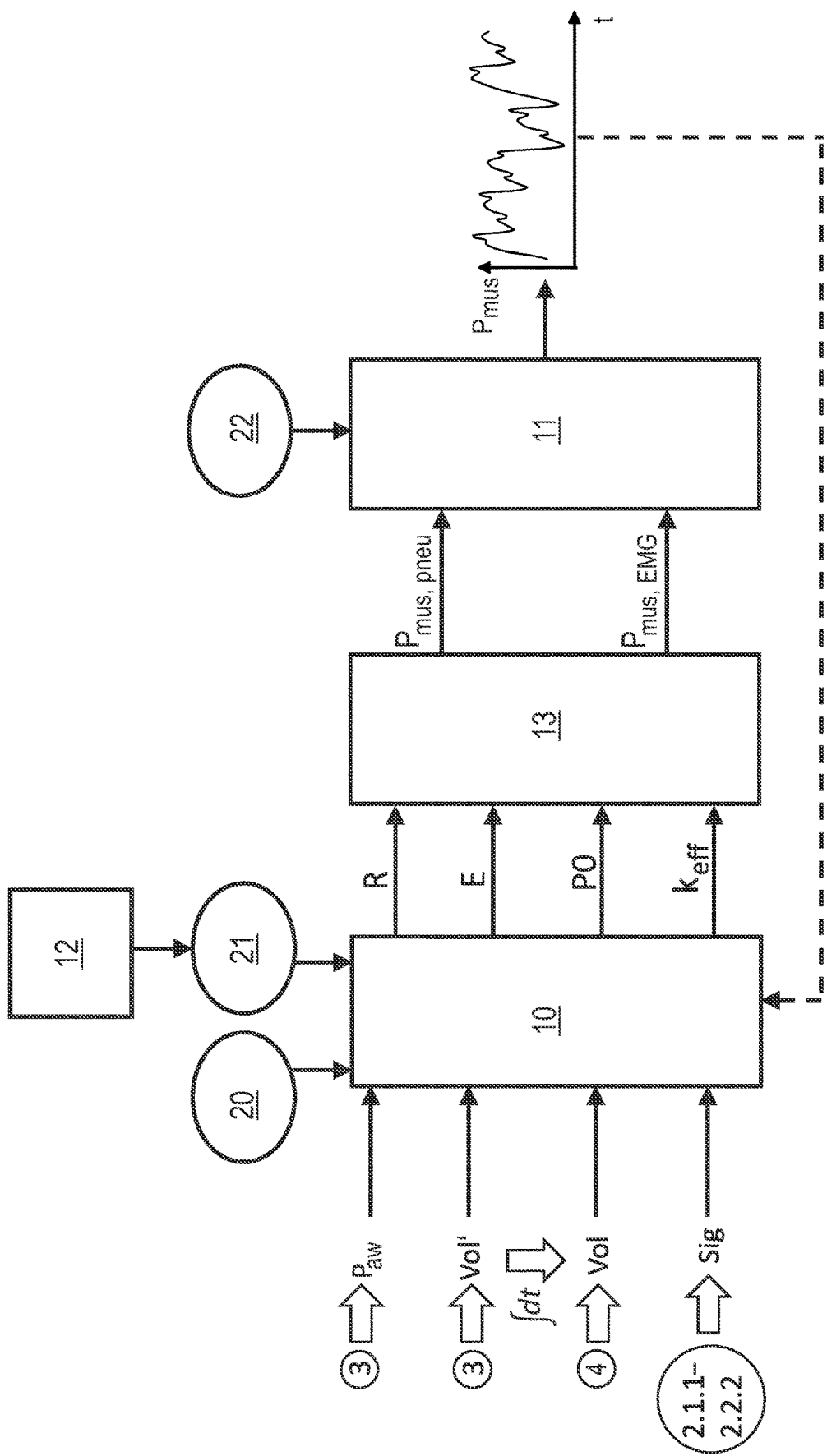
FIG. 3 is a schematic view showing an additional estimator, which automatically combines two estimations determined in different ways for the pneumatic parameter $P_{mus}$.

FIG. 3 shows another variant. The parameter estimator 10 yields estimated values for the model parameters R, E, P0 and $k_{eff}$, of which there are four in this case. An additional $P_{mus}$ estimator 13 located upstream of the $P_{mus}$ estimator 11 proper calculates a pneumatically determined estimation $P_{mus,pneu}(k)$ on the basis of the model equation (1), and, on the other hand, an electrically determined estimation $P_{mus,EMG}(k)$ on the basis of the model equation (8). The $P_{mus}$ estimator 11 proper calculates an aggregation, especially an averaging, via these two estimations determined in different ways. In one embodiment, the $P_{mus}$ estimator 11 proper uses an additional Kalman filter, which uses, for example, the following state space equation:

$$\underline{x}(k+1) = \underline{I} * \underline{x}(k) + \underline{\varepsilon}(\text{"Random Walk"}) \text{ with} \quad (38)$$

$$\underline{x}(k) = \begin{pmatrix} P_{mus,pneu}(k-1) \\ P_{mus,EMG}(k-1) \end{pmatrix} \quad (39)$$

$$\underline{I} = \begin{pmatrix} 1 & 0 \\ 0 & 1 \end{pmatrix} \quad (40)$$

and $$\underline{\varepsilon} = \begin{pmatrix} \varepsilon 1 \\ \varepsilon 2 \end{pmatrix} \quad (41)$$

wherein ε is a parameter for the measurement error: What error is inherently present in the two estimations $P_{mus,pneu}(k)$ and $P_{mus,EMG}(k)$ for the pneumatic parameter $P_{mus}$?

Figure 4:
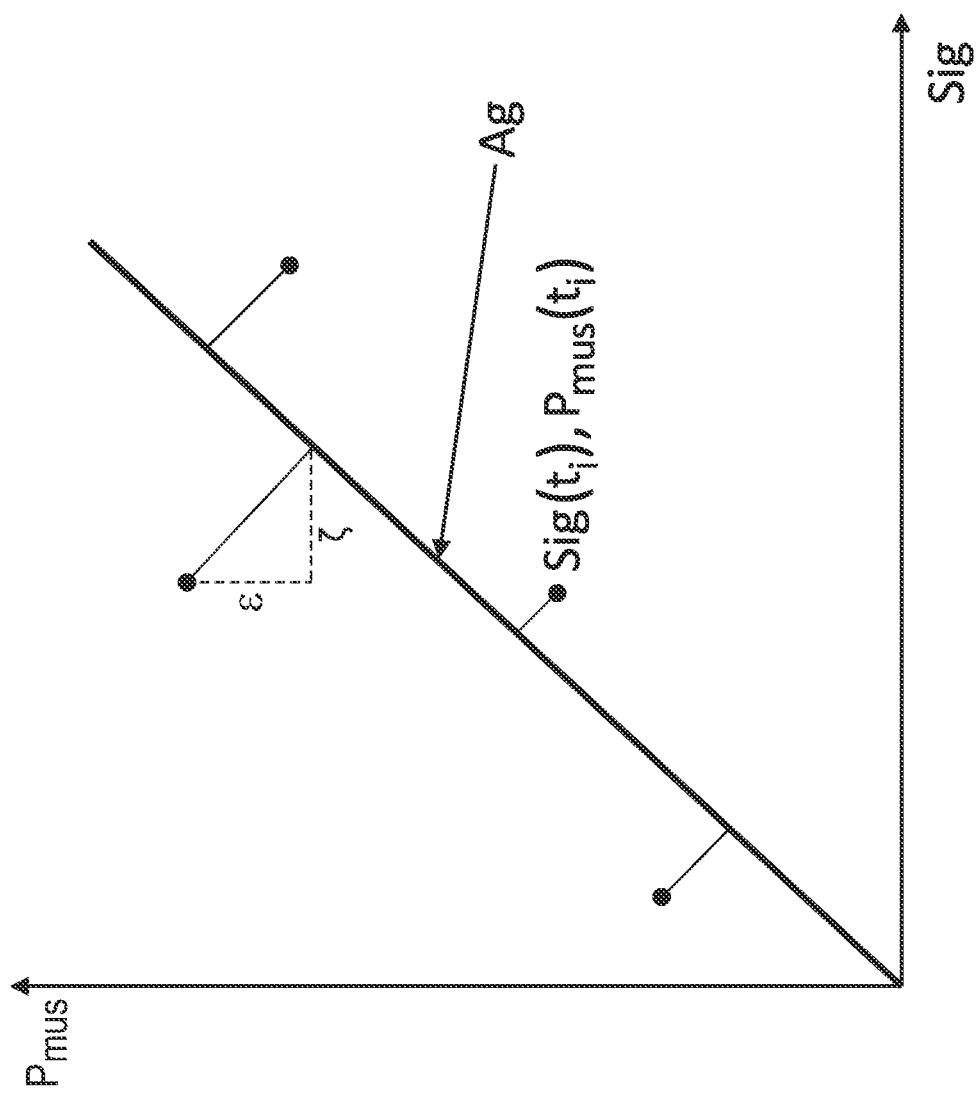
FIG. 4 is a graph showing an example of how the process noise and the measurement noise are taken into account.

In one form of implementation, this embodiment leads to the following minimization task: Preset is the model equation $P_{mus}$, wherein c describes the process noise (deviation between model and reality) and ζ describes the measurement noise (measurement error during the generation of the signal Sig). For a scanning time window, $k_{eff}$ is considered to be constant over time. A signal value tuple $\{Sig(t_i), P_{mus,est}(t_i)\}$ is generated for a plurality of scanning times $t_i$. For example, $P_{mus,est}(t_i)$ is estimated with the use of the model equation (1). A best fit line Ag is then drawn by calculation through the signal value tuple. The sum of the distances between the signal value tuples and the best fit line Ag is minimized, doing so in a direction at right angles to the best fit line Ag and not in a direction at right angles to the x axis. FIG. 4 shows this in a two-dimensional coordinate system with Sig on the x axis and with the estimated parameter $P_{mus}$ on the y axis.

The weightings 21, which the parameter estimator 10 uses, and the mode of operation of the weighting estimator 12 will be described in more detail below. In one embodiment, the sensor array with the electrodes (EMG sensors) 2.1.1 through 2.2.2 yield the electrical respiratory signal Sig. These sensors are arranged relatively close to the source for the electrical signals in the body of the patient P. Therefore, no weighting factors are used in one embodiment for the values of the signal Sig.

The sensors 7, 4 and 6 measure pneumatic variables, and the sensors 7 and 4 and 6 are located at a relatively great distance from the source for the breathing activity in the body of the patient P. The following description pertains to an embodiment in which the sensors 2.2.1, . . . , 2.2.2 or 6 or 14, 7 and 4 yield measured values at each scanning time t, and the signal processing unit 5 generates from these measured values a triple with three signal values {Sig(t), Vol'(t), Vol(t)}.

It is also possible to generate a quadruple {$Sig_1(t)$, $Sig_2(t)$, Vol'(t), Vol(t)}.

For each signal value triple/quadruple and for each scanning time the weighting estimator 12 calculates a weighting factor σ(t) each. The parameter estimator 10 receives weighted signal values, e.g., each receives a triple {α($t_i$)*Sig($t_i$), α($t_i$)*Vol'($t_i$), α($t_i$)Vol($t_i$).

It is also possible to use different weightings for the signal values of a triple, e.g., {$α_1$*α(t)*Sig(t), $α_2$*α(t)*Vol'(t), $α_3$*α(t)*Vol(t)}, wherein the weighting factors $α_1$, $α_2$, $α_3$ are preset in advance and are constant over time.

It is also possible to scale the variance of the summand $\underline{\sigma}_n$ for the measurement noise inversely with the weighting factor: $\underline{\sigma}_{n,w}(t) = \underline{\sigma}_n/α(t)$. The weighting factor α(t) is considered here to be variable over time.

The following basic principle is preferably valis: The higher the information content, the higher is the weighting α(t) of such a signal value triple. In one embodiment, the information content of a triple increases with decreasing frequency of occurrence of that triple in a random sample, i.e., in a set of signal value triples. In another embodiment, such triples in which one of the three signal values has a markedly greater relative amplitude than the other two signal values are provided with a high weight. The relative amplitude is defined, for example, as the deviation of the signal value from the arithmetic mean or from the median of all measured values for this signal.

In one embodiment, a set of signal value triples is generated for a sequence of scanning times. An empirical density estimation is carried out with a set of signal value triples as the random sample in a three-dimensional space, for example, in a Cartesian coordinate system with the three coordinate axes Sig, Vol' and Vol or in a polar coordinate space. For example, the three-dimensional space is divided into areas, e.g., cuboids, and a respective frequency is calculated for each area of the three-dimensional space. Each signal value triple in this area receives a weighting, which is, e.g., equal to the reciprocal value of the estimated frequency of the area.

Freak values and obviously incorrect measured values are preferably removed automatically, doing so before the values for the model parameters are determined and before the weighting factors just described are calculated. Triples with freak values or with incorrect measured values are prevented hereby from receiving a high weight. Threshold values (limits) or ranges for measured values with a physiological and/or anthropological significance are preferably preset in order to detect freak values and incorrect measured values. It is also possible to recognize freak values and incorrect measured values by means of statistical methods. Triples with freak values and/or with incorrect measured values are sorted out or they receive the weighting factor zero or a very low weighting factor.

While specific embodiments of the invention have been shown and described in detail to illustrate the application of the principles of the invention, it will be understood that the invention may be embodied otherwise without departing from such principles.

LIST OF REFERENCE NUMBERS

| | |
|---|---|
| 1 | Ventilator; it ventilates the patient P mechanically; comprises the signal processing unit 5 and the memory 9 |
| 2.1.1, 2.1.2 | First set of measuring electrodes on the skin of the patient P; it provides measured values for the electrical respiratory signal Sig, which is correlated with the pneumatic parameter $P_{mus}$, they are EMG sensors |
| 2.2.1, 2.2.2 | Second set of measuring electrodes on the skin of the patient P, closer to the diaphragm Zw; providing additional measured values for the electrical respiratory signal Sig, which is correlated with the pneumatic parameter $P_{mus}$, they are EMG sensors |
| 3 | Connection piece with an image recording device and with an image processing unit; it measures the geometry of the body of the patient P in the thoracic region, from which the current filling level of the lungs, Vol, is derived |
| 4 | Optical sensor with an image recording device and with an image processing unit; it measures the geometry of the body of the patient P in the thoracic region, from which the current filling level of the lungs, Vol, is derived |
| 5 | Signal processing unit; it carries out the steps of the process according to the present invention; it has read access to the memory 9 |
| 6 | Probe in the esophagus Sp; it measures the pneumatic pressure $P_{es}$ in the esophagus Sp; it is in fluid connection with the measuring catheter 8 |
| 7 | Pneumatic sensor in front of the mouth of the patient P; it measures the volume flow Vol' and the airway pressure $P_{aw}$ |
| 7.1 | Transducer of sensor 2; it taps air from the fluid connection between the lungs Lu of the patient P and the ventilator 1 |
| 7.2 | Pressure sensor proper of the sensor 7; it receives measured values from the transducer 7.1 |
| 8 | Measuring catheter in the esophagus Sp |
| 9 | Memory, in which the lung-mechanical model 20 and the gradient model 22 are stored and to which the signal processing unit 5 has read access |
| 10 | Parameter estimator; it has read access to the lung-mechanical model 20; provides values for the model parameters of the lung-mechanical model 20; it optionally uses weightings 21 |
| 11 | $P_{mus}$ estimator proper; it has read access to the gradient model 22; receives estimated values for the model parameters of the lung-mechanical model 20; provides the estimated pneumatic parameter $P_{mus}$ |
| 12 | Weighting estimator; it provides weightings 21 as a function of frequencies of signal values |
| 13 | Upstream additional $P_{mus}$ estimator; it provides two different estimations $P_{mus, pneu}(k)$ and $P_{mus, EMG}(k)$ |
| 14 | Gastric probe in the stomach Ma of the patient P; it measures the gastric pressure $P_{ga}$ |
| 20 | Lung-mechanical model; it indicates at least one relationship between the pneumatic parameter $P_{mus}$ and a plurality of measurable signals for a respective scanning time; it preferably comprises a plurality of model equations with model parameters; it is stored in the memory 9 |
| 21 | Weightings for the signal value sets; calculated by the weighting estimator |
| 22 | Gradient model for the pneumatic parameter $P_{mus}$ over a plurality of scanning times; stored in the memory 9 |
| $\alpha(t_i)$ | Weighting factor for a signal value set at the scanning time $t_i$ |
| Ag | Best fit line in a two-dimensional coordinate system with Sig as the x axis and $P_{mus}$ as the y-axis |
| E | Model parameter in the form of a lung-mechanical factor; elasticity of the lungs of the patient P |
| $k_{eff}$ | Neuromuscular efficiency of the respiratory muscles of the patient P; it is a model parameter |
| Ma | Stomach of the patient P; it receives the gastric probe 14 |
| P | Patient with the esophagus Sp, with the stomach Ma and with the diaphragm Zw; ventilated mechanically by means of the ventilator 1 from time to time |
| P0 | Model parameter in the form of a lung-mechanical summand: Residual pressure after complete exhalation by the patient P |
| $P_{aw}$ | Airway pressure, generated by a superimposition of the spontaneous breathing of the patient P to the mechanical ventilation by the ventilator 1; it is measured by the sensor 3 |
| $P_{es}$ | Pressure in the esophagus Sp of the patient P; it is measured with a probe 6 in the esophagus Sp |
| $P_{mus}$ | Pneumatic parameter to be determined for the spontaneous breathing of the patient P |
| $P_{mus, EMG}(k)$ | Estimated value for the pneumatic parameter $P_{mus}$; determined by analysis of signals from the measuring electrodes 2.1.1 through 2.2.2 (EMG signal) |
| $P_{mus, pneu}(k)$ | Estimated value for the pneumatic parameter $P_{mus}$, determined by analysis of signals from the pneumatic sensors 3, 4 and 6 |
| $P_{mus, est}(t_i)$ | Approximately determined value of the pneumatic parameter $P_{mus}$ for the scanning time $t_i$ |
| R | Model parameter in the form of a lung-mechanical factor: Breathing resistance, which the airways of the patient P offer to the volume flow Vol' |
| Sig | Electrical respiratory signal, generated from measured values from the measuring electrodes 2.1.1 through 2.2.2 |
| Sp | Esophagus of the patient P; it receives the optional probe 6 |
| $t_k$ | Vector with N scanning times |
| Zw | Diaphragm of the patient P |

What is claimed is:

1. A process comprising the steps of:
presetting a computer-analyzable lung-mechanical model which describes at least one relationship between a pneumatic parameter to be determined and one or more of:
 a volume flow signal for a flow of breathing air to and/or from the lungs of the patient; and
 a volume signal for a filling level of the lungs of the patient; and
 a measurable pneumatic pressure signal for pressure in airways or in an esophagus of the patient; and
 a respiratory signal correlated with the spontaneous breathing of the patient;
presetting a computer-evaluable gradient model for the pneumatic parameter, wherein the gradient model describes a value of the pneumatic parameter for a scanning time as a function of at least N values of a variable, which is variable over time and which is correlated with the pneumatic parameter for N previous scanning times, wherein N is a preset number, and automatically generating, with a data-processing signal processing unit, a respective signal value for at least one signal to which the lung-mechanical model refers; and during the generation of the signal values, with the signal processing unit, receiving measured values from an airway pressure sensor and/or from an esophageal pressure sensor and/or from a volume flow sensor and/or from a volume sensor and based on the measured values generating one or more of the volume flow signal and the volume signal and the measurable pneumatic pressure signal;

during the generation of the signal values, with the signal processing unit, receiving sensor array measured values from a sensor array on skin of the patient and generating the respiratory signal from the sensor array measured values;

with the signal processing unit, determining N respective values for any variable that is correlated with the pneumatic parameter and appears in the gradient model for N consecutive scanning times; and with the signal processing unit, determining a respective value for the pneumatic parameter during a subsequent use phase for at least one scanning time, wherein the signal processing unit uses for the determination of the respective value for the pneumatic parameter during the subsequent use phase at least:

generated signal values for the scanning time;

respective, already determined N values of the correlating variable of the gradient model for N previous scanning times;

the lung-mechanical model; and the gradient model, wherein the signal processing unit provides the pneumatic parameter as input to a ventilator for synchronizing operation of the ventilator with spontaneous breathing of a ventilated patient based on the pneumatic parameter.

2. A process in accordance with claim 1, wherein:

during the subsequent use phase, in the step of determining a value of the pneumatic parameter for at least one scanning time, the signal processing unit uses at least one preset computer-evaluable Kalman filter, which comprises the gradient model; and a sequence of N values of the correlating variable or of each correlating variable of the gradient model is used as a component of a state vector of the Kalman filter for N consecutive scanning times.

3. A process in accordance with claim 1, wherein:

during the subsequent use phase, in the step of determining a value of the pneumatic parameter for a scanning time, the signal processing unit uses a preset computer-analyzable second Kalman filter, which comprises the lung-mechanical model; and values for the pneumatic parameter and values for one or more of the volume flow signal and the volume signal and the respiratory signal are used as components of an observation equation of the Kalman filter.

4. A process in accordance with claim 1, wherein:

during the subsequent use phase, in the step of determining a value of the pneumatic parameter for a scanning time, the signal processing unit uses at least one preset computer-analyzable Kalman filter, which comprises both the gradient model and the lung-mechanical model;

a sequence of N values of the correlating variable or of each correlating variable of the gradient model for N consecutive scanning times and values for at least one of the volume flow signal and of the volume signal and of the pneumatic pressure signal and of the respiratory signal are used as components of an observation equation of the Kalman filter.

5. A process in accordance with claim 1, wherein the preset lung-mechanical model comprises:

a first relationship between the pneumatic parameter as well as one or more of the volume flow signal and the volume signal and the pneumatic pressure signal; and a second relationship between the pneumatic parameter and the respiratory signal, wherein the signal processing unit:

determines a respective first value and a second value for the pneumatic parameter for N scanning times during the subsequent use phase;

uses the first relationship as well as at least one respective value of the volume flow signal and of the volume signal and of the measurable pneumatic pressure signal for the determination of the first value for the scanning time; and uses the second relationship as well as at least one value of the respiratory signal for the determination of the second value for the scanning time; and uses, during the subsequent use phase in the step of determining a value of the pneumatic parameter for a scanning time:

the N first values;
the N second values; and
the gradient model.

6. A process in accordance with claim 1, wherein when no value is available for a signal occurring in the lung-mechanical model at a scanning time, the value of the pneumatic parameter is determined for said scanning time exclusively with the use of the gradient model.

7. A process in accordance with claim 1, wherein the gradient model describes the value of the pneumatic parameter at the scanning time as a function of N values of the correlating variable for N previous scanning times as well as additionally of the respective value of at least one measurable variable at the scanning time.

8. A process in accordance with claim 1, wherein the preset lung-mechanical model comprises at least one model parameter, which is variable over time, wherein during the subsequent use phase, in the step of determining a value of the pneumatic parameter for a scanning time, the signal processing unit calculates a respective model parameter value with the use of signal values for said scanning time and of signal values for at least one earlier scanning time for at least one model parameter, which is variable over time, and additionally determines at least one value for the pneumatic parameter with the use of the calculated model parameter value of each calculated model parameter value.

9. A process in accordance with claim 1, wherein during an initialization phase, the signal processing unit determines N values of the variable correlating with the pneumatic parameter for N consecutive scanning times with the use of generated signal values.

10. A process in accordance with claim 1, wherein the signals comprise one or more of an EMG signal acquired by one or more sensors on skin of the patient, an MMG signal acquired by one or more sensors on skin of the patient, and a pneumatic signal generated by a sensor in the body of the patient.

11. A process in accordance with claim 1, further comprising providing a computer program, which is executed on the signal processing unit, upon the signal processing unit receiving measured values from at least one of the airway pressure sensor, the esophageal pressure sensor, the volume flow sensor, the volume sensor and the sensor array, wherein an execution of the computer program on the signal processing unit causes the signal processing unit to carry out at least some of the process steps.

12. A process in accordance with claim 1, wherein a signal sequence, comprising commands to be executed on the signal processing unit causes the signal processing unit to carry out at least some of the process steps upon the signal processing unit receiving measured values from at least one of the sensor array for measuring the spontaneous breathing of the patient, and from the airway pressure sensor and from the esophageal pressure sensor and from the volume sensor.

13. A signal processing unit for an approximate automatic determination by calculation of a pneumatic parameter for spontaneous breathing of a patient, the signal processing unit comprising:
a processor comprising at least occasional read access to a memory with a stored computer-analyzable lung-mechanical model and a stored computer-analyzable gradient model for the pneumatic parameter, wherein:
the lung-mechanical model describes at least one relationship between the pneumatic parameter and one or more of a volume flow signal for a flow of breathing air to and/or from the lungs of the patient, and a volume signal for a filling level of the lungs of the patient and a measurable pneumatic pressure signal for pressure in the airways or in an esophagus of the patient and a respiratory signal which is correlated with the spontaneous breathing of the patient;
the gradient model describes a value of the pneumatic parameter for a scanning time at least as a function of N values of a variable, which is variable over time and is correlated with the pneumatic parameter for N previous scanning times, wherein N is a preset number;
the processor is configured to generate a respective signal value repeatedly for at least one signal to which the lung-mechanical model refers,
the processor is configured to receive measured values from at least one of an airway pressure sensor and an esophageal pressure sensor and a volume flow sensor and a volume sensor to generate from the received measured values the volume flow signal and the volume signal and the pressure signal and measured values from a sensor array which measures a variable that is correlated with the spontaneous breathing of the patient, and a second sensor array on the skin of the patient and from a sensor in the body of the patient when generating the signal values;
the processor is configured to determine, during an initialization phase, N values of the variable or each variable correlating with the pneumatic parameter and occurring in the gradient model for N different scanning times;
the processor is further configured to determine in a subsequent use phase a respective value for the pneumatic parameter for at least one scanning time,
the processor is configured to use for this determination during the subsequent use phase at least:
generated signal values for the at least one scanning time;
respective, already determined N values of the variable or each variable of the gradient model, which variable is correlated with the pneumatic parameter, for N previous scanning times,
the lung-mechanical model; and
the gradient model;
the processor is configured to provide the pneumatic parameter as output to a ventilator for synchronizing operation of the ventilator with the spontaneous breathing of the patient.

14. A system comprising the signal processing unit in accordance with claim 13, and further comprising the ventilator, wherein the ventilator is configured:
to ventilate a patient mechanically; and
to use the pneumatic parameter for the spontaneous breathing of the patient for the mechanical ventilation, wherein the pneumatic parameter used has been determined by the signal processing unit.

15. A system in accordance with claim 14, wherein:
during the subsequent use phase, the signal processing unit uses at least one preset Kalman filter, which comprises the gradient model, for the determining of a value of the pneumatic parameter for at least one scanning time; and
a sequence of N values of the correlating variable or of each correlating variable of the gradient model is used as a component of a state vector of the Kalman filter for N consecutive scanning times.

16. A system in accordance with claim 14, wherein:
during the subsequent use phase, for determining a value of the pneumatic parameter for a scanning time, the signal processing unit uses a preset second Kalman filter, which comprises the lung-mechanical model; and
values for the pneumatic parameter and values for one or more of the volume flow signal and the volume signal and the respiratory signal are used as components of an observation equation of the Kalman filter.

17. A system in accordance with claim 14, wherein:
during the subsequent use phase, for determining a value of the pneumatic parameter for a scanning time, the signal processing unit uses at least one preset Kalman filter, which comprises both the gradient model and the lung-mechanical model;
a sequence of N values of the correlating variable or of each correlating variable of the gradient model for N consecutive scanning times and values for at least one of the volume flow signal and of the volume signal and of the pneumatic pressure signal and of the respiratory signal are used as components of an observation equation of the Kalman filter.

18. A system in accordance with claim 14, wherein the lung-mechanical model comprises:
a first relationship between the pneumatic parameter as well as one or more of the volume flow signal and the volume signal and the pneumatic pressure signal; and
a second relationship between the pneumatic parameter and the respiratory signal, wherein the signal processing unit:
determines a respective first value and a second value for the pneumatic parameter for N scanning times during the subsequent use phase;
uses the first relationship as well as at least one respective value of the volume flow signal and of the volume signal and of the measurable pneumatic pressure signal for the determination of the first value for the scanning time; and
uses the second relationship as well as at least one value of the respiratory signal for the determination of the second value for the scanning time; and uses, during the subsequent use phase in the step of determining a value of the pneumatic parameter for a scanning time:
the N first values;
the N second values; and
the gradient model.

19. A system in accordance with claim 14, wherein the preset lung-mechanical model comprises at least one model parameter, which is variable over time, wherein during the subsequent use phase, in the step of determining a value of the pneumatic parameter for a scanning time, the signal processing unit calculates a respective model parameter value with the use of signal values for said scanning time and of signal values for at least one earlier scanning time for at least one model parameter, which is variable over time, and determines at least one value for the pneumatic parameter with the use of the calculated model parameter value.

20. A system in accordance with claim 14, wherein during the initialization phase, the signal processing unit determines N values of the variable correlating with the pneumatic parameter for N consecutive scanning times with the use of generated signal values.

* * * * *